United States Patent [19]

Fehmi et al.

[11] 4,031,883
[45] June 28, 1977

[54] MULTIPLE CHANNEL PHASE INTEGRATING BIOFEEDBACK COMPUTER

[75] Inventors: Lester G. Fehmi, Princeton, N.J.; Joseph R. Schneider, Larchmont, N.Y.

[73] Assignee: Biofeedback Computers, Inc., Rocky Point, N.Y.

[22] Filed: July 21, 1976

[21] Appl. No.: 707,480

Related U.S. Application Data

[62] Division of Ser. No. 492,954, July 29, 1974, Pat. No. 3,978,847.

[52] U.S. Cl. .......................... 128/2.1 B; 128/2.1 M
[51] Int. Cl.² ........................................ A61B 5/04
[58] Field of Search ......... 128/2.1 B, 2.1 M, 2.1 R, 128/2.1 Z

[56] References Cited

UNITED STATES PATENTS

| | | | |
|---|---|---|---|
| 3,032,029 | 5/1962 | Cunningham | 128/2.1 B |
| 3,034,500 | 5/1962 | Backster, Jr. | 128/2.1 B |
| 3,495,596 | 2/1970 | Condict | 128/2.1 B |
| 3,753,433 | 8/1973 | Bakerich et al. | 128/2.1 B |
| 3,774,593 | 11/1973 | Hakata et al. | 128/2.1 B |
| 3,821,949 | 7/1974 | Hartzel et al. | 128/2.1 B |

Primary Examiner—William E. Kamm
Attorney, Agent, or Firm—Allison C. Collard

[57] ABSTRACT

Multiple monopolar electrical contacts are applied to the scalp or body, using other points on the body as reference and ground. The brain muscle or other bioelectric waves conducted from each contact, relative to the reference point, are amplified, filtered, and instantaneously analyzed to produce a signal which may be perceived by the person or persons generating the bioelectric waves. This sensory feedback signal simultaneously may communicate to the generating party or parties the ongoing fluctuations in frequency, amplitude, and phase unity among two or more biological rhythms occuring within an individual, couple, or group of persons. The feedback signal may be used as an aid to establish awareness and control over the functions monitored, as an aid to meditation, as an aid to learning to flexibly and easily establish or dissolve the various states of attention and consciousness associated with the signaled characteristics of the monitored brainwaves or muscle potentials and as an aid to communicaton between neural systems within a person, i.e., lobes of the brain, muscle groups or between other nonverbal biological activities of two or more persons being monitored.

17 Claims, 3 Drawing Figures

MULTIPLE CHANNEL PHASE INTEGRATING BIOFEEDBACK COMPUTER

This is a division of application Ser. No. 492,954, filed on July 29, 1974, now Pat. No. 3,978,847.

This invention relates to a multi-channel electromyographic (EMG) and electroencephalographic (EEG) feedback training apparatus and a system for brain wave and muscle potential analysis for use on human trainees.

Bio-feedback training is a recently developed technique by which persons may learn to control physical processes of the body. In bio-feedback training, the participant is informed by means of a sensory signal such as a tone or a light, of the state of a particular aspect of his body's functionin, e.g., the level of muscle tension, blood pressure, temperature, or the frequency and amplitude of his brain waves. By using the information contained in the feedback signal, reflecting changes in the monitored physiological process, the trainee can gradually learn to control the monitored functions.

One of the physiological functions which have been investigated using bio-feedback training techniques is electroencephalographic (EEG) activity. The EEG records small changes in voltage on the cortex of the brain, through recording electrodes placed on the human scalp. EEG activity is recorded from electrodes placed on the five lobes of the brain. EEG recordings show four distinctive brain wave patterns in human subjects. These waves are distinguished and categorized according to the amplitude and frequency of fluctuation of the voltage. Different types of EEG brain wave patterns have been found to be associated with different attentional states. High frequency (above 13 Hz), low amplitude, brain wave activity, called "beta" activity, is associated with a state of narrowly focussed attention, high arousal, tension, and anxiety. Lower frequency (8–13 Hz), high amplitude activity, called "alpha" activity, is associated with a state of relaxed wakefullness, in which attention is diffused to include a broader field of one or more sense modalities, simultaneously. These two types of activity are present in the EEG records of most waking humans, in varying amounts. Lower frequency (4–8 Hz), high amplitude waves, called "theta" waves, are associated with creative imagery and daydreaming, and occur in most humans before falling asleep or as they are arousing from sleep. "Delta" waves (1–4 Hz) are high amplitude waves normally occurring only during sleep.

The verbal reports of subjects who receive biofeedback training and who achieve brain wave control often include statements which associate various EEG parameters to states of self-consciousness, attention, and concentration. Thus, viewed within the context of these reports, the development of control over brain wave states, that is, intentionally increasing and decreasing amplitude and frequency of brain wave activity, is linked with an increase in attentional flexibility.

Most research in EEG bio-feedback found in the prior art has involved training subjects to control their alpha wave activity. Consistent with the fact that alpha is associated with a state of relaxed wakefullness, trainees who have learned to increase their production of alpha wave activity have reported feeling more integrated, and less tense after bio-feedback training. As the amplitude of alpha wave activity grows larger, trainees report experiences of timelessness, energy, unity, and unself-consciousness. The implications of these changes to all areas of the trainee's behavior are profound.

Bio-feedback training of varius physiological functions for example electromyographic (EMG) activity, has recently been developed also as a training technique useful in the mitigation of various physical symptoms, such as migraine headaches and tension. EEG bio-feedback training has been observed as a mitigator of various neurotic physiological conditions, such as anxiety, depressions, compulsive behavior, and stress reactivity, as well as a mitigator of some physiological symptoms, such as nausea, dizziness, tension, body discomfort, headaches, and other psychosomatic symptoms. Thus, EFG bio-feedback training may be used to treat specific symptoms, although the majority of the trainees have been normal individuals interested in developing their attentional capacity or generally exploring with a view toward enhancing their potential.

The typical trainee is comfortably seated in a darkened, sound-attenuated room. He closes his eyes and beings to hear a sound which occurs when he is producing alpha waves. By letting his mind go through various mental states which naturally change in most persons, the trainee begins to sense the association of his various mental states with the presence and absence of the tone. Gradually, the trainee begins to be able to control the tone. He learns to change these mental states at will, as well as to sustain certain states for longer periods of time. The development of this control allows the trainee to become more aware of many aspects of his varied mental states, patterns of the changes in the mental states, timing of the changes, the mental processes precipitating the changes, etc. More importantly, by learning to sustain the tone for a length of time, the trainee can directly experience the dimensions of consciousness associated with the parameters of the brain waves which generate the feedback tone.

The training experience itself is a gentle process, in that the trainee himself has complete control over the changes which occur during the training sessions. Therefore, the rate of learning to control brain waves varies among the subjects. Those trainees having a subtle awareness of their internal processes and an interest in discovering how to manipulate the tone learn quickly. More timid, less aware or motivated trainees learn more slowly.

Successful trainees generally describe the subjective experience associated with the feedback signal in terms which are very similar to each other. The most dramatic subjective effects associated with the production of alpha activity occur during the initial period following a sudden and sustained increase in alpha duration or amplitude which takes place simultaneously at all five recording sites. The pleasant aspects of this experience appear to be associated with the feeling of release which accompanies an increase in amplitude and abundance of alpha activity.

When a new alpha level is reached predominantly on one lobe of the brain, while the other lobes remain for the most part at their previous low-alpha levels, the subjective experience is more subtle and more difficult to discern. Verbal reports suggest, however, that the alpha activity of each lobe, as signaled by feedback to the subject, has associated with it a unique experimental content. However, it is not a common event to find increases in alpha occurring in only one lobe of the brain without corresponding small increases in alpha occurring in the other lobes. That is, increasing alpha production on any of the five lobes of the brain tends to simultaneously produce increases on the other lobes.

Another electrophysiological parameter which has been discovered is the phase agreement of EEG activity simultaneously recorded from different brain loci. When two waves are rising and falling in synchrony, they are termed "in-phase", while they are described as being "out-of-phase" if the voltages are changing in opposite direction. After a 20-minute exposure to a feedback tone which signaled when the right and left occipital rhythms were within 15° of being exactly in-phase, ten trainees demonstrated an ability to increase and decrease phase agreement with respect to their performance before they received training. These results were statistically significant, while there was no control of phase agreement demonstrated by control trainees who received feedback which was not contingent upon phase agreement of their brain waves. The results of these studies are also relevant to attentional mechanisms. The verbal reports from the trainees and 87 pilot subjects associate the occurrence of the feedback tone, which reflects phase agreement, with their being aware of a relatively stable mental image. When this one-pointedness of mental focus was disrupted, the phase agreement between occipital waves was lost. These findings are general to the entire range of EEG frequencies which were monitored.

The EEG recordings during phase agreement showed relatively high levels of alpha activity. In terms of physiological parameters, alpha amplitude may be directly related to ease of achieving phase agreement. The occipital waves of certain subjects were observed to be more in-phase when emitting large amplitude bursts of alpha activity. In general, the alpha rhythm was the most prominent brain rhythm displayed in the EEC records of the subjects used in the experiment.

The EEG fedback system of the present invention has remote experimenter consoles, containing five independent data channels, electrode and battery test functions indicated by meter needle deflections, plug in filter modules which determine the frequency of five pole elipitical filters with approximately 24 db per actave rolloff, and digital filters for each channel. The consoles contain an on-off switch for each channel, additional 60 Hz notch filters (40 db attenuation), and a counter for each channel which registers the percent of time that brain wave activity exceeds a preset adjustable threshold. The counter can also indicate an integral of the energy generated for that activity channel in a given test period. There is a counter reset for all channels, and gain and threshold controls for each channel. In addition, the consoles contain a summing amplifier, and an output meter to indicate the energy of the phase sensitive resultant of any combination of channels of input activity. This energy measure thus simultaneously reflects the rate of occurrence, amplitude and phase relations of EEG activity from a large area of the brain. A channel selector switch provides access to the summing amplifier output and to the outputs from each of the five channels for oscilloscope monitoring or other functions. A threshold gain control adjusts the level at which the feedback tone, representing the averaged EEG activity, becomes audible. The feedback tone reflects the frequency and amplitude of the averaged signal as well as the degree of phase agreement of input activity to the summing amplifier.

Any channel combinations for feedback may be selected. Each channel has the capacity to produce a feedback tone individually and simultaneously with each other and with the average EEG channel.

Unlike EEG biofeedback devices which employ only analog filtering techniques, the instrument of the invention may combine analog and digital filtering techniques. It can select any band pass between 2 and 10,000 Hz for transmission (extended range is optional), providing complete rejection of frequencies outside the band pass. Frequency analysis of other than the dominant frequency in the EEG is one of the reasons that make combined analog/digital filtering a necessity in a research or clinical instrument.

The multi-channel design of this instrument allows it to serve as a frequency analyser to determine the energy contained in each of five separate and preset frequency bands of any EEG wave form over a range of preselected periods. The multi-channel design also permits the simultaneous analysis of frequency, amplitude (or energy), and phase relatedness of as many as five distinct EEG wave forms simultaneously. Analyses may be performed independently of whether or not amplitude, frequency and phase contingent feedback is utilized. Feedback is not delayed in time after first period or cycle of activity, and is presented audibly and visually instantaneously as it occurs.

The invention as it is embodied in FIGS. 1 and 2 while primarily designed to monitor and give multi-channel feedback training and provide analysis of brain waves contains all the necessary components to monitor and give multiple channel feedback training, and provide analysis, of muscle potentials. The frequency band width of myographic activity is from 90 to 10,000 Hz. The special advantages offered by the present device in EMG training derive from existing knowledge regarding the distribution of tension in the body. Body tension often does not entail tension in just one muscle or one group of muscles. Body tension may be and often is reflected by tension in many groups simultaneously. Thus, existing single channel EMG feedback systems fail to reflect systemic stress while a multiple channel device such as the one described herein may be used to detect and reflect the level of tension of widely distributed muscles simultaneously. In the latter case one tone instantaneously represents the average tension level in microvolts of as many channels of muscle activity as are being recorded from. Each individual muscle activity level is displayed on the integrated energy meter for each channel and the averaged muscle activity across all monitored channels is displayed by the summing channel energy meter. When an auditory feedback signal is utilized, for example, the feedback tone decreases in frequency as tension levels and muscle potentials diminish.

A problem which has long existed in EEG biofeedback and in EEG recording in general has been electrode attachment. The procedure has required a careful and time consuming application of electrodes, usually employing a paste or gel which presented clean-up problems after sessions and subject discomfort. Such procedures were necessary to provide low electrode resistances (10k ohms) for a usable EEG signal which is free of 60 Hz and other unwanted electrical activity. The quality of the preamplifiers (110 db common mode rejection) and a 60 Hz notch filter (40 db attenuation) make possible the use of a simple and paste-free electrode system. Thus, electrode attachment is an easy and rapid (45 seconds total time) procedure for the experimenter or clinician, and a comfortable experience for the subject, without unnecessary paste residual.

Other features which make this instrument easy to use and effective are its internal electrode test, battery test, and calibration systems. An adjustable oscillator provides a push button check of electrode resistance without polarizing the electrodes. This oscillator also provides a calibration signal for the entire system and thus, serves as a means by which the integrity of the system may be checked as well as the amplitude, frequency and phase response of each channel.

Display meters can be set to reflect on-going activity or activity integrated over an internally timed duration which is selectable from 15 seconds to 32 minutes. After the timed duration ends, meters stop and hold their position indefinitely until reset, while the feedback tone continues uninterrupted.

It is therefore an object according to the present invention to provide a multi-channel biofeedback method and apparatus in which persons may learn to control the physical processes of their body by means of a sensory signal which is responsive to the state of a particular aspect of a person's functioning.

It is another object according to the present invention to provide a method and apparatus for the measurement of biofeedback activity in a person which is simple in design and reliable in operation.

Other objects and features of the invention will become apparent from the following detailed description considered in connection with the accompanying drawings which disclose the embodiments of the invention. It is to be understood however that the drawings are designed for the purpose of illustration only and not as a definition of the limits of the invention.

In the drawings wherein similar reference characters denote similar elements throughout the several views.

Figure 1:
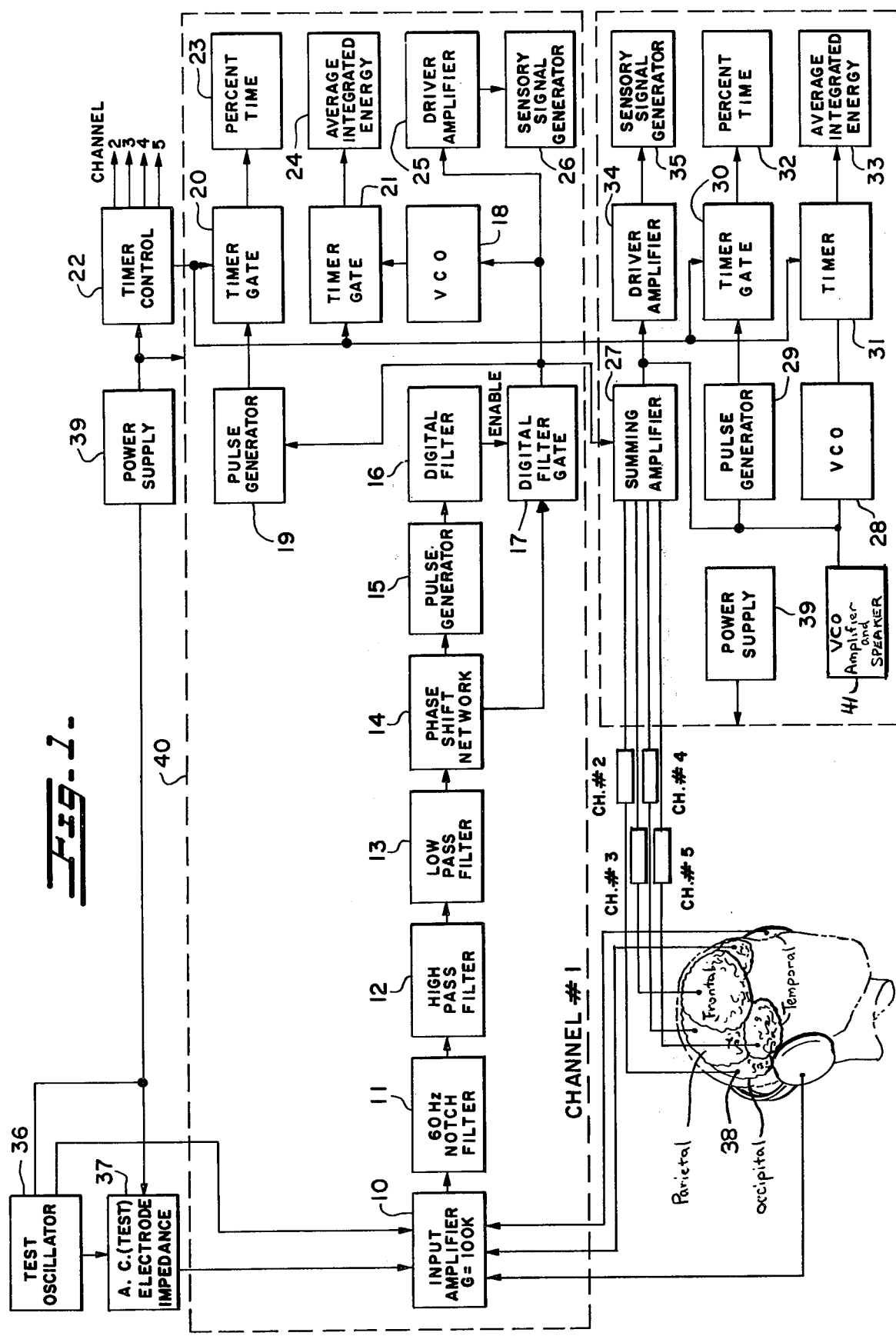
FIG. 1 is a schematic block diagram of the electrical circuitry illustrating the apparatus of the subject invention.

Referring to FIG. 1 input amplifier 10 is a preamplifier and consists preferably of a differential amplifier having a minimum of one megohm input impedance. The gain is variable between 10K to 100K, and there is approximately 110 db common mode rejection. The input bias current is less than 2.0 nanoamperes. Inputs are derived from scalp electrodes 38. The output is fed to a 60 Hz notch filter 11. Notch filter 11 has approximately 40 db rejection of unwanted 60 Hz signals. Its 3 db band width is approximately 3 Hz. The variable 10K to 100K gain on the preamplifier allows the operator to equalize channel gains at optimum meter display valves. In addition, other feedback gain controls are provided in order to "weight" the desired channels in order to optimize feedback for individuals who produce very large signals on only one or two channels. In this case, the large signals would ordinarily dominate the feedback production. Reducing the effect of large signals so that the activity from the five major lobes can all be approximately equally reflected in the phase integrated feedback is the function of the "weighting" control.

The outlet of notch filter 11 is coupled to a high pass filter 12. High pass filter 12 is a five pole eliptical filter, with 24 db roll off per octave. In its present configuration, the 3 db pass frequencies may be varied by changing five resistors in the filter circuit, by means of a five wafer, multi-position switch or by means of an interchangeable plug in. The range of this filter is from 2 to 80 Hz. The output is delivered to a low pass filter 13. Low pass filter is also a five pole eliptical filter with 24 db roll off per octave. In its present configuration, the 3 db down frequencies may be varied by changing five resistors in the filter circuit, by means of a five wafer, 10 position switch or by means of an interchangeable plug in. The range of the filter is from 2 to 80 Hz. The output from the low pass filter is fed to a phase shift network 14.

Phase shifting network 14 permits the phase relation of the brain wave signal to be adjusted with respect to the other channels of brain wave activity, over a range of 360 degrees. The phase relations of all channels can thus be equalized and auditory feedback can be presented in any specified phase relation to neural activity.

Therefore, the shifting of the phase of the amplified signals with respect to the occurrence of brain wave activity permits the sensory signal to have an impact on the brain which is in phase with the occurrence of subsequent brain wave activity. The output from the phase shifting network is coupled to a pulse generator 15. Generator 15 is a trigger circuit and feeds uniform amplitude pulses to a digital filter circuiit for period analysis. Amplified, analog filtered, and phase shifted brain waves from network 14 trigger the production of these uniform pulses when these brain waves cross the zero voltage level in the positive going direction. The output from the pulse generator is fed into a digital filter 16.

Filter 16 performs a period analysis upon the input pulses from pulse generator 15, and opens signal gate 17 when the input pulses fall between high and low period durations, which may be preset or manually adjusted. The range of the digital filter is between 2 and 80 Hz. The digital filter provides uniform voltage output for in-band frequencies and total rejection of out-of-band frequencies. The absolute accuracy of the digital filter is 0.5 Hz, and the frequency resolution is 0.50 Hz.

Digital filter gate 17 controls the passage of the amplified and filtered brain wave signal from phase shift network 14 to a summing amplifier 27, a voltage controlled oscillator 18, a pulse generator 19, and a sonalert amplifier 25. Gate 17 is opened for a time equal to the direction of the longest preset period, this time commencing at the instant that the period criteria are satisfied by the preceeding pulses in digital filter 16. Gate 17 controls the passage of present real time brain wave signals, not pulses. The brain wave activity which is delivered to subsequent circuitry is, in fact, the activity occurring during the period after the period duration criteria have been met. Since brain wave activity tends to occur in bursts, consisting of repetitive trains of identical frequency activities, the likelihood of occurrence of the desired frequencies at approximately the same time that the criterion is met is quite high.

The combination of eliptical and digital filtering results in feedback which is both immediate and accurate. The combination filtering accentuates desired frequencies for which feedback is desirable. Information or feedback concerning the presence of the desired frequency is provided in greater abundance than if the signal had not been analog filtered first since in the latter case, the digital filter would reject circumstances during which both the desired and undesired frequencies were present at the same time. By pre-filtering out the undesired frequencies, the present system maximizes the desired frequencies, the sharp band pass cutoffs are possible.

Voltage controlled oscillator (VCO) 18 receives filtered brain wave activity from digital filter gate 17 and delivers pulses at a frequency which is directly proportional to the amplitude of the input brain wave activity to a timer gate circuit 21. Ultimately, these pulses are summed to produce an integrated energy and display 24 measure of brain wave activity. Pulse generator 19 receives filtered brain wave activity from digital filter gate 17, and delivers a single pulse of uniform amplitude for each brain wave which satisfies the preselected criterion of amplitude, to the timer gate 20, and, subsequently, to a percent time circuit and display meter 23.

Timer gate 20 opens when the start switch of the timer is activated and closes at the end of the timed cycle. When opened, the timer enables passage of the input from pulse generator 19 to the percent time circuit 23. This function depends upon the operation of th timer, which is explained with reference to timer control 22. Timer gate 21 opens when the start switch of the timer is activated, and closes at the end of the timed cycle. When opened, timer 21 enables passage of the input from voltage controlled oscillator 18 to an average integrated energy counter 24. This function depends upon the operation of a timer control 22.

A driver amplifier 25 receives input brain wave activity from the digital filter gate 17. This amplifier permits adjustment of the brain wave amplitude threshold for the onset of sensory signal production and adjustment of the sensory signal intensity volume. The output from the diver amplifier is delivered to sensory signal generator 26. The sensory signal generator 26 may be a commercially available device or speaker which delivers a 400 Hz carrier frequency tone that is volume modulated by the amplitude of the input signal. Thus, a tone whose volume rises and falls in accordance with the rise and fall of the voltage in each cycle is heard by the person whose brain waves are being monitored.

The summing amplifier 27 receives its input from digital filter gate 17. Summing amplifier 27 accepts inputs from one channel, or any combination of the five channels of brain wave activity as shown, depending upon the position of the switches on the input to the summing amplifier. At the output, an instantaneous algebraic sum of input activity is delivered to the driver amplifier 34, voltage controlled oscillator 28, and pulse generator 29. Five auxilliary inputs to the summing amplifier (not shown) will permit simultaneous training of two persons using the same feedback tone.

The following is an examle of how the summing amplifier operates on two waves to produce the sum or average activity shown below:

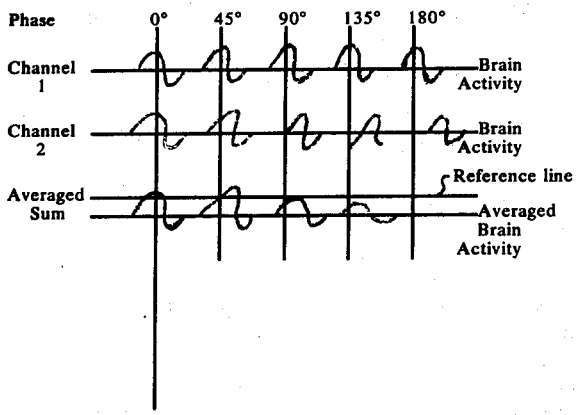

If the reference line represents the threshold for the production of the feedback signal, then it is possible to see how the phase synchrony is related to feedback production. Only the 0° and the 45° signals of averaged brain activity exceed the threshold for feedback signal production. From this example, it is easy to extrapolate to cases where there are more than two waves, and particularly five channels of information. The use of a logarithmic or other non-linear amplifier which preferentially amplifies large amplitudes over small amplitudes will permit the control of how much the monitored waves may be out of phase and still produce a feedback tone.

Voltage controlled oscillator 28 receives it input from summing amplifier 27, and delivers pulses at a frequency which is directly proportional to the amplitude of the input to timer gate circuit 31.

Timer gate 31 opens when the start switch of the timer 22 is activated and closes at the end of the timed cycle. When opened, the timer gate enables passage of the output of from the voltage controlled oscillator 28 to the average integrated energy counter 33. This function depends upon the operation of the timer 22. Ultimately, these pulses are summed to produce a phase integrated energy measure of brain wave activity which is displayed 33.

Pulse generator 29 receives its input from summing amplifier 27, and delivers a single pulse of uniform amplitude for each input wave which satisfies the preselected criterion of amplitude to timer gate 30 and, subsequently, to the percent time circuit 32. Timer gate 30 opens when the start switch of the timer is activated, and closes at the end of the timed cycle. When the gate is opened, the timer enables passage of the output from pulse generator 29 to the percent time circuit 32. This function depends upon the operation of timer 22.

The percent time circuit 32 is an analog device which counts and sums the input pulses of uniform amplitude from pulse generator 29 via timer gate 30, over a 5 second time constant, and displays the results on a meter. Thus, this display represents the average percent of time that the summed brain were activity is present in the band of frequencies which have been preselected by filters 12, 13, 16 of the individual channels.

Average integrated energy circuit 33 is a digital device which sums the input pulses from voltage controlled oscillator 28 via timer gate 31 and displays on a meter or counter, the average energy score in microwatts which were recorded for the period determined by timer control 22.

The driver amplifier 34 receives its input from summing amplifier 27. The driver amplifier permits adjustment of the wave amplitude threshold for the onset of sensory signal production, and adjustment of the signal intensity or volume. The output from the driver amplifier is delivered to the sensory signal genertor 35, which has the same circuit as sensory signal generator 26 described earlier.

The test oscillator 36 produces a sinusoidal wave from which is selectable from 2 to 80 Hz in one Hz steps, and has an amplitude which is selectable from six available values: 4, 8, 16, 32, 64, and 128 microvolts. The test oscillator delivers output to the A.C. electrode impedance test circuit 37, and to input amplifier 10 for system calibration and trouble shooting.

The electrode test function 37 measures the A.C. electrode contact impedance of each placement at any desired frequency available from oscillator 36. When the electrode test button is depressed, a sinusoidal signal from test oscillator 36 is impressed upon the recording electrode with respect to the ground electrode and the current is monitored on a meter. The contact impedance is displayed on a meter. A contact impedance of 40 ohms or less is considered necessary under most conditions for an optimum function of the machine.

Each electrode 38 consists of a felt pad wetted with a combination salt and alcohol solution, which is fastened to a metal wire, and leads to the input circuit of the amplifier. The high quality of input amplifiers 10, and the 60 Hz notch filter 11 make possible the use of this simple electrode system without paste. The ground and reference electrodes are mounted on plastic ear clips which are clipped on the ears during recording periods. Five recording electrodes are held in contact to the person's scalp by means of a two-piece headband which is constructed from an elastic waist band and Velcro. The main piece of the headband fits around the head; the second piece fits across the top of the head and is held in place by Velcro contact to the main piece. The electrodes are slipped under the headband to make scalp contact. The five electrode sites are mid-frontal (middle of forehead about 1 inch below the hair line), midoccipital (middle of the back of the head about one inch above the inion), mid-parietal (middle of the top of the head at the vertex), right temporal (even with the middle of the right ear, about 1 inch above the top of the right ear), and left temporal (even with the middle of the left ear, about 1 inch above the top of the left ear).

Power supply 39 preferably consists of two 12-volt lantern or automobile storage batteries or a DC voltage generating system. Voltage is regulated to plus or minus 8 volts throughout the system. A meter on the preamplifier console is provided which constantly monitors the + and − 12 volt battery supply.

Each complete channel 40 of which there are five or more, receives inputs from electrodes 38, test oscillator 36, and the timer control circuit 22, which enables and disables the counters and meters (23 and 24). Each channel gives an input to the summing amplifier 27, and also drives a counter 24, meter 23, and sonalert 26. The rms noise of each channel is less than 1.0 microvolt. The output of each of the five channels combines analog and digital filtering techniques, which results in accurate and instantaneous feedback delivery.

The multi-channel design of this phase integrating, feedback encephalograph and spectral analyzer permits the simultaneous analysis of frequency, amplitude (or energy) and phase relatedness of five distinct EEG wave forms from the five major lobes of the brain simultaneously. Analyses may be performed independently of whether or not amplitude, frequency, and phase contingent feedback is utilized. When each channel is preset to filter separate and contiguous frequency ranges, than the unit can be utilized as a five channel spectral analyzer. Variable 10 to 100 K gain on each of the input amplifiers 10 allows the operator to equalize channel gains at optimum meter display values. In addition, other feedback gain controls are provided in order to weight the output of individual channels as desired, so that certain low energy waves may produce proportionally more feedback signal than would otherwise be the case. The feedback tone may be delivered from each channel individually, from the summed output, or from any combination of the two modes. The system provides outputs including the summer biofeedback tone outputs, 5 individual channel biofeedback tone outputs, unfiltered pre-amplifier outputs, filtered outputs, summer amplifier output, and 6 percent time and integrated energy meter displays.

Figure 3:
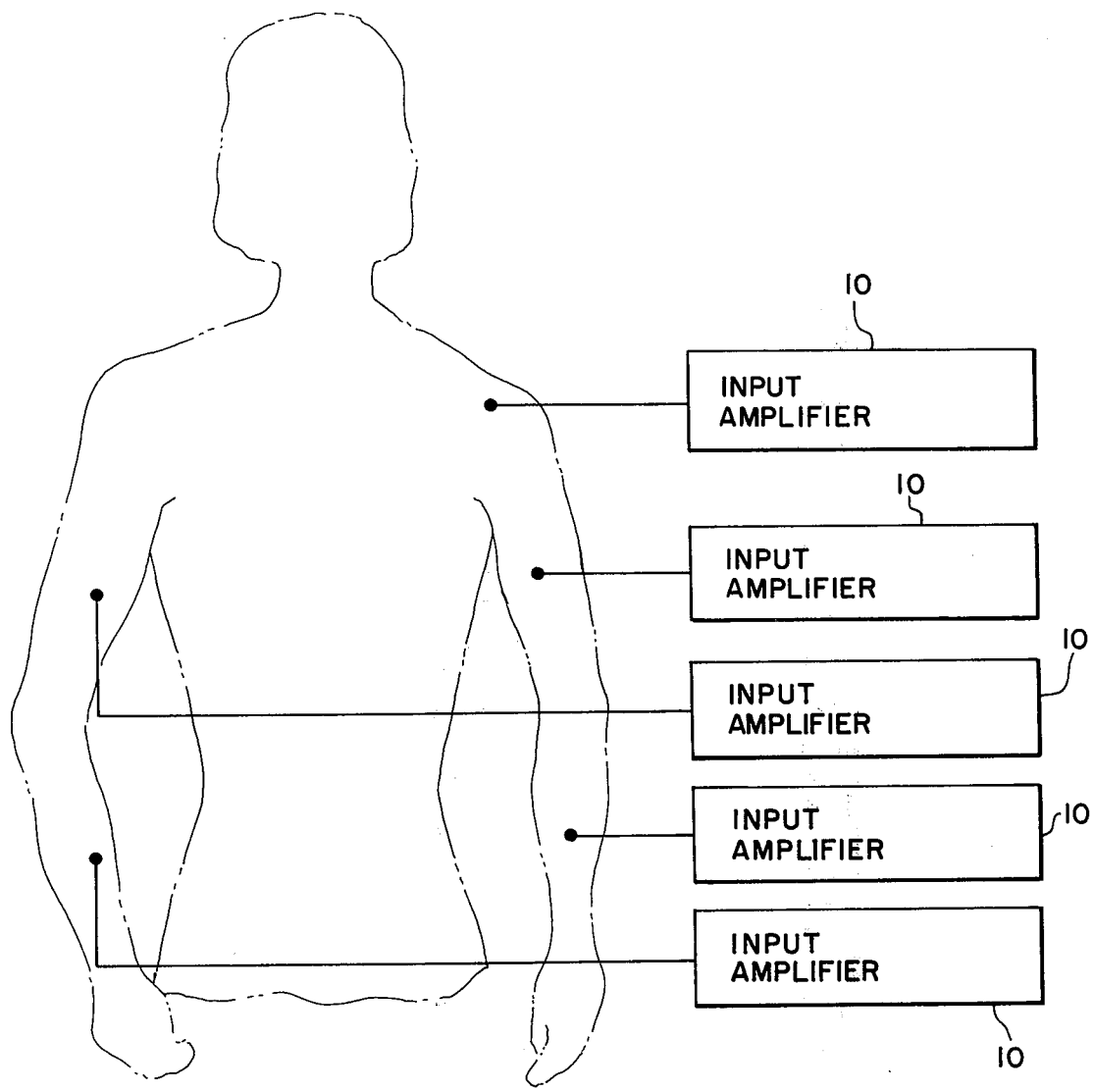
FIG. 3 is a view of a trainee having sensors connected to muscle areas of the body.

The use of this device as an averaging electromyoraphic (muscle activity) feedback computer is accomplished by directing a mode selector switch to the EMG position which connects the suming amplifier to a VCO amplifier and speaker module 41. Module 41 permits the selection of a threshold for feedback which is appropriate for the particular magnitude of average muscle activity being monitored. Module 41 also permits selection of the appropriate time constant of integration over which the muscle activity accumulates to produce the feedback signal (see FIG. 3).

Figure 2:
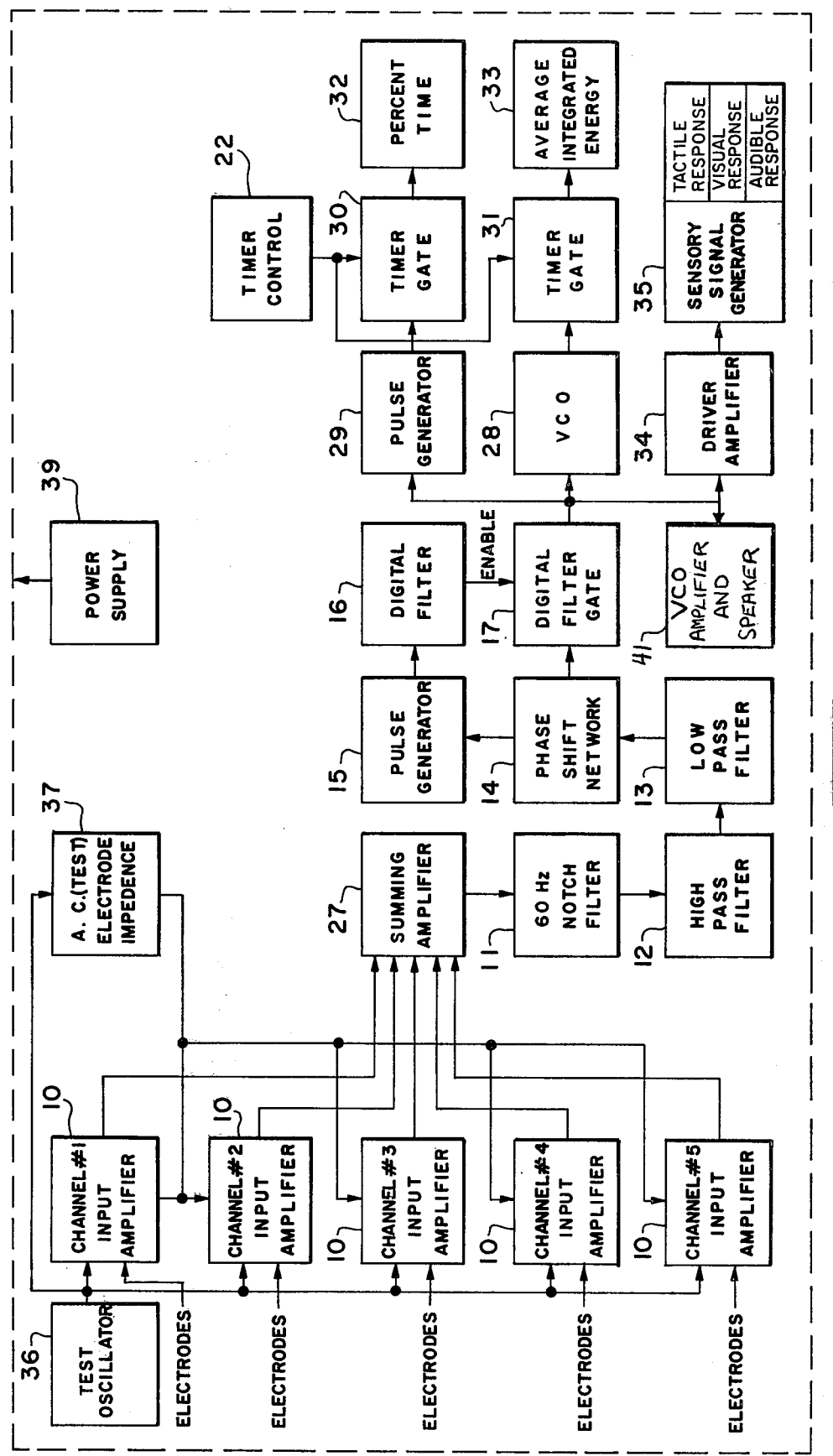
FIG. 2 is another embodiment of a simpler apparatus of the invention illustrated in a schematic block diagram.

FIG. 2 discloses another embodiment of a five channel phase integrating feedback encephalograph and electromyograph which is of a simpler design than in the embodiment of FIG. 1. This simpler embodiment uses some of the same circuits in a different arrangement and identical circuits are given the same reference numerals as those shown in FIG. 1.

In the embodiment of FIG. 2, the five electrodes from the patient are connected to the inputs of five amplifiers 10. Each of the outputs of amplifiers 10 are fed into the input of a summing amplifier 27 whose output is an instantaneous algebraic sum of the input activity of the brain. The output of the summing amplifier is then coupled through filters 11, 12 and 13, phase shift network 14 and pulse generator 15 in a manner similar to FIG. 1. The operation of the remaining circuit elements which have identical numbers to the elements of FIG. 1 is the same as the description provided for FIG. 1 so that the percent time 32, the average integrated energy 33 and the sound tone from the sonalert 35 and be observed. The circuit of FIG. 2 eliminates the requirement of having a repetition of five separate channels each containing filters and meter circuitry since summing amplifier 27 has been moved forward to receive the outputs of the amplifiers directly. This simplified version of the circuit of FIG. 1 however does not permit one to measure the individual parameters of each of the five areas of the brain, since these are immediately combined in summing amplifier 27. For some purposes, however, this simplified version would be satisfactory and result in a substantial savings in cost and space.

To further reduce costs, albeit with reduced filtering capacity, the digital filter may be removed from the circuit. That is, pulse generator 15, digital 16 and digital filter gate 17 may be omitted. Thus, the simplified version would operate exclusively with analog filtering. Various units, e.g., 11, 12, 13 and 14, may be utilized in various sequences without affecting the desired result.

One through five channels or any combination of input channels may be provided as an input to the summing amplifier depending upon the position of the input switches. The apparatus of the subject invention can record phase sensitive energy spectra, that is, can provide information regarding the phase relations for the different frequencies of brain wave or their activity. Most spectrum analyzers provide indices of the amount of energy within various frequency bands. The apparatus of the present invention accomplishes this and in addition, provides an index of the amount of the in-phase energy within any preset frequency band. Spectrum energy and in-phase spectral energy may be useful as a diagnostic indicator of integration of unity of mental and physical processes. It appears from various tests that people who function poorly or feel poorly will show low in-phase energy scores.

Percent time or integrated energy may be used as a criteria for the presentation of materials to be learned. It is not unlikely that optimum learning occurs during inphase energy states and therefore learning ability may be greatly enhanced by training students to increase in-phase brain wave energy. Moreover, the material to be learned may be programmed to be presented automatically by the present device only when the brain waves meet criteria for in-phase energy. This may be accomplished by the closure of relay contacts when the threshold criteria for in-phase energy are reached and maintained.

It is also possible to train two or more persons with the same feedback signal so that they have to produce alpha waves simultaneously in order to hear the feedback signal. They both would also have to meet phase criteria as well. That is, amplitude, frequency and phase criteria are required to be simultaneously met by both persons in order for the feedback signal to be presented. This training to increase the brain wave synchrony has the application of enhancing communications between two or more persons such as business, social or marriage partners.

Aside from the audible tone which can be used as the sensory feedback response to the human subject, vibrator can also be used. The vibrator would increase power of stroke with an increase in amplitude and phase relatedness and it would increase the frequency of stroke with the frequency of brain waves. In addition, to the use of an audible tone and/or vibrator as the sensory feedback response to the human subject a light can be used. The light, for example, would increase in brightness with an increase in amplitude and phase relatedness and it would increase in stroboscopic frequency as the frequency of the brain waves increase. Alternately the light can be made to turn on and remain on as long as amplitude and phase criteria continue to be met.

While only a few embodiments of the present invention have been shown and described, it will be obvious that many changes and modifications may be made thereunto without departing from the spirit and scope of the claims.

What is claimed is:

1. An apparatus for measuring the electroencephalographic activity of at least two lobes of the brain of a human trainee and providing the trainee with a sensory signal in response to a combination of amplitude and the inphase activity of each of the brain lobes comprising:
    a plurality of electrical contacts coupled to the head of the trainee, said contacts being disposed adjacent to at least two lobes or areas of the brain, and to a neutral area of the trainee's head for obtaining at least two signals from said contacts which correspond to each of said at least two lobes or areas of the brain;
    at least one amplifier for amplifying said at least two signals;
    filter means coupled to said at least one amplifier for filtering the signals to obtain output signals each within a defined frequency range;
    a summing amplifier coupled to said filter means for summing the in-phase signals of the defined frequency band of the amplified brain wave activity to produce a phase relevant measure of the trainee's brain wave activity;
    audio signal means coupled to said summing amplifier for producing an auditory signal and modulating the volume of the auditory signal responsive to the amplitude and phase of the summed brain wave activity, so as to present to the trainee an audible signal which reflects the degree of phase parity and amplitude of the signals recorded from said at least two lobes or areas of the brain.

2. The apparatus as recited in claim 1 additionally comprising a phase shifter following said filter means for shifting the phase of the amplified signals with respect to the occurrence of the brain wave activity so that the occurrence of the sensory signal may be adjusted so that its impact on the brain is in phase with the occurrence of subsequent brain wave activity.

3. The apparatus as recited in claim 2 comprising a pulse generator coupled to said phase shifter for producing uniform pulses responsive to the phase so that a uniform voltage output is produced for signals having frequencies that are within the band width of said filter means.

4. The apparatus as recited in claim 3 comprising a digital filter having its input coupled to said pulse generator for digitally filtering said uniform voltage output so as to detect the frequency of brain wave activity within the defined frequency range and a digital filter gate coupled to said digital filter for passing the filtered brain wave acitivity to said summing amplifier when the brain wave frequency is within the defined range.

5. The apparatus as recited in claim 4 comprising a counter and integrator coupled to the output of said digital filter gate for counting and integrating pulses generated from the brain wave activity and display means for displaying the average percent of time that the brain wave activity is present in the band of frequencies selected by said filter means, so that the trainee is presented the energy present in the band of frequencies selected by said filter means.

6. The apparatus as recited in claim 1 comprising a counter and integrator coupled to the output of said summing amplifier for displaying the average percent time that the in-phase brain wave activity is present in the band of frequencies selected by said filter means, and obtaining and displaying the in-phase energy present in the band of frequencies selected by said filter means.

7. An apparatus for measuring the electroencephalographic activity of at least two lobes of the brain of a human trainee and providing the trainee with a sensory signal in response to a combination of amplitude and the in-phase activity of each of the brain lobes comprising;
    a plurality of electrical contacts coupled to the head of the trainee, said contacts being disposed adjacent to at least two lobes or areas of the brain, and to a neutral area of the trainee's head for obtaining at least two signals from said contacts which correspond to each of said at least two lobes or areas of the brain;

at least one amplifier for amplifying said at least two signals;

a summing amplifier coupled to said amplifier for summing the in-phase signals of the amplified brain wave activity to produce a phase relevant measure of the trainee's brain wave activity;

filter means for filtering the summed signals to obtain an output signal within a defined frequency range;

audio signal means for producing an auditory signal and modulating the volume of the auditory signal responsive to the amplitude and phase of the summed brain wave activity so as to present to the trainee an audible signal which reflects the degree of phase parity and amplitude of the signals recorded from said at least two lobes or areas of the brain.

8. An apparatus for measuring the electroencephalographic activity of at least two lobes of the brain of a human trainee and providing the trainee with a sensory signal in response to a combination of amplitude and the in-phase activity of each of the brain lobes comprising:

a plurality of electrical contacts for coupling to the head of the trainee, said contacts being disposed adjacent to at least two lobes or areas of the brain, and to a neutral area of the trainee's head so as to obtain at least two signals from said contacts which correspond to each of said at least two lobes or areas of the brain;

at least one amplifier for amplifying said at least two signals;

filter means coupled to said amplifier for filtering each of the signals to obtain output signals each within a defined frequency range;

a summing amplifier coupled to said filter means for summing the in-phase signals of the defined frequency band of the amplified brain wave activity to produce a phase relevant measure of the trainee's brain wave activity; and signal means for producing a tactile signal and modulating the magnitude of the tactile signal responsive to the amplitude and phase of the summed brain wave activity so as to present to the trainee the tactile signal which reflects the degree of phase parity and amplitude of the signals recorded from said at least two lobes or areas of the brain.

9. An apparatus for measuring the electroencephalographic activity of at least two lobes of the brain of a human trainee and providing the trainee with a sensory signal in response to a combination of amplitude and the in-phase activity of each of the brain lobes comprising:

a plurality of electrical contacts for coupling to the head of the trainee, said contacts being disposed adjacent to at least two lobes or areas of the brain, and to a neutral area of the trainee's head so as to obtain at least two signals from said contacts which correspond to each of said at least two lobes or areas of the brain;

at least one amplifier coupled to said contacts for amplifying said at least two signals;

filter means coupled to said amplifier for filtering each of the signals to obtain output signals each within a defined frequency range;

a summing amplifier coupled to said filter means for summing the in-phase signals of the defined frequency band of the amplified brain wave activity to produce a phase relevant measure of the trainee's brain wave activity; and signal means for producing a visual signal and modulating the brightness of the visual signal responsive to the amplitude and phase of the summed brain wave activity so as to present to the trainee the visual signal which reflects the degree of phase parity and amplitude of the signals recorded from said at least two lobes or areas of the brain.

10. An apparatus for measuring the electroencephalographic activity of at least two lobes of the brain of a human trainee and providing the trainee with a sensory signal in response to a combination of amplitude and the in-phase activity of each of the brain lobes comprising:

a plurality of electrical contacts for coupling to the head of the trainee, said contacts being disposed adjacent to at least two lobes of areas of the brain, and to a neutral area of the trainee's head so as to obtain at least two signals from said contacts which correspond to each of said at least two lobes or areas of the brain;

at least one amplifier coupled to said contacts for amplifying said at least two signals;

a summing amplifier coupled to said at least one amplifier for summing the in-phase signals of the amplified brain wave activity to produce a phase relevant measure of the trainee's brain wave activity;

filter means coupled to said summing amplifier for filtering the summed signals to obtain an output signal within a defined frequency range; and signal means coupled to said filter means for producing a tactile signal and modulating the magnitude of the tactile signal responsive to the amplitude and phase of the summed brain wave activity so as to present to the trainee the tactile signal which reflects the degree of phase parity and amplitude of the signals recorded from said at least two lobes or areas of the brain.

11. An apparatus for measuring the electroencephalographic activity of at least two lobes of the brain of a human trainee and providing the trainee with a sensory signal in response to a combination of amplitude and the in-phase activity of each of the brain lobes comprising:

a plurality of electrical contacts for coupling to the head of the trainee, said contacts being disposed adjacent to at least two lobes of areas of the brain, and to a neutral area of the trainee's head so as to obtain at least two signals from said contacts which correspond to each of said at least two lobes or areas of the brain;

at least one amplifier coupled to said contacts for amplifying said at least two signals;

a summing amplifier coupled to said at least one amplifier for summing the in-phase signals of the amplified brain wave activity to produce a phase relevant measure of the trainee's brain wave activity;

filter means coupled to said summing amplifier for filtering the summed signals to obtain an output signal within a defined frequency range;

signal means coupled to said filter means for producing a visual signal and modulating the brightness of the visual signal responsive to the amplitude and phase of the summed brain wave activity so as to present to the trainee the visual signal which reflects the degree of phase parity and amplitude of the signals recorded from said at least two lobes or areas of the brain.

12. An apparatus for measuring the bioelectrical activity such as muscle activity of at least two regions of the body of a human trainee and providing the trainee with a sensory signal corresponding to the amplitude and in-phase activity of each of the regions of the body comprising:

a plurality of electrical contacts for coupling to the body of the trainee, said contacts being disposed adjacent to at least two regions of the body, and to a neutral area of the trainee's body;

at least one amplifier coupled to said contacts for amplifying said at least two signals;

filter means coupled to said amplifier for filtering the signals to obtain an output signal within a defined frequency range;

a summing amplifier coupled to said filter means for summing the amplified signals to produce a phase relevant measure of the trainee's bioelectrical activity; and signal means coupled to said summing amplifier for producing a tactile signal and modulating the magnitude of the tactile signal responsive to the amplitude and phase of the summed bioelectrical activity so as to present to the trainee the tactile signal which reflects the degree of phase parity and amplitude of the signals recorded from said at least two body regions.

13. An apparatus for measuring the bioelectrical activity such as muscle activity of at least two regions of the body of a human trainee and providing the trainee with a sensory signal corresponding to the amplitude and in-phase activity of each of the regions of the body comprising:

a plurality of electrical contacts for coupling to the body of the subject, said contacts being disposed adjacent to at least two regions of the body, and to a neutral area of the trainee's body so as to obtain at least two signals from said contacts which correspond to each of said at least two regions of the body;

at least one amplifier coupled to said contacts for amplifying said at least two signals;

filter means coupled to said at least one amplifier for filtering the signals to obtain an output signal within a defined frequency range;

a summing amplifier coupled to said filter means for summing the amplified signals to produce a phase relevant measure of the trainee's bioelectrical activity; and signal means coupled to said summing amplifier for producing a visual signal and modulating the brightness of the visual signal responsive to the amplitude and phase of the summed bioelectrical activity so as to present to the trainee the visual signal which reflects the degree of phase parity and amplitude of the signals recorded from said at least two body regions.

14. An apparatus for measuring the bioelectrical activity such as muscle activity of at least two regions of the body of a human trainee and providing the trainee with a sensory signal correspnding to the amplitude and in-phase activity of each of the regions of the body comprising:

a plurality of electrical contacts for coupling to the body of the trainee, said contacts being disposed adjacent to at least two regions of the body, and to a neutral area of the trainee's body so as to obtain at least two signals from said contacts which correspond to each of said at least two regions of the body;

amplifier means for amplifying said at least two signals;

filter means coupled to said amplifier for filtering the signals to obtain an output signal within a defined frequency range;

a summing amplifier for summing the amplified signals to produce a phase relevant measure of the trainee's bioelectrical activity; and audio signal means for producing an auditory signal and modulating the volume of the auditory signal responsive to the amplitude and phase of the summed bioelectrical activity so as to present to the trainee an auditory signal which reflects the degree of phase parity and amplitude of the signals recorded from said at least two body regions.

15. An apparatus for measuring the bioelectrical activity such as muscle activity of at least two regions of the body of a human trainee and providing the trainee with a sensory signal in response to a combination of amplitude and the inphase activity of each of the regions of the body comprising, a plurality of electrical contacts for coupling to the body of the trainee, said contacts being disposed adjacent to at least two regions of the body, and to a neutral area of the trainee's body so as to obtain at least two signals from said contacts which correspond to each of said at least two regions of the body;

at least one amplifier coupled to said contacts for amplifying said at least two signals;

a summing amplifier coupled to said at least one amplifier for summing the in-phase signals of the amplified signals to produce a phase relevant measure of the trainee's bioelectrical activity;

filter means coupled to said summing amplifier for filtering the summed signals to obtain an output signal within a defined frequency range; and signal means coupled to said filter means for producing a tactile signal and modulating the magnitude of the tactile signal responsive to the amplitude and phase of the summed bioelectrical activity so as to present to the trainee and tactile signal which reflects the degree of phase parity and amplitude of the signals recorded from said at least two regions of the body.

16. An apparatus for measuring the bioelectrical activity such as muscle activity of at least two regions of the body of a human trainee and providing the trainee with a sensory signal in response to a combination of amplitude and the in-phase activity of each of the regions of the body comprising, a plurality of electrical contacts for coupling to the body of the trainee, said contacts being disposed adjacent to at least two regions of the body, and to a neutral area of the trainee's body so as to obtain at least two signals from said contacts which correspond to each of said at least two regions of the body;

at least one amplifier coupled to said contacts for amplifying said at least two signals;

a summing amplifier coupled to said at least one amplifier for summing the in-phase signals of the amplified signals to produce a phase relevant measure of the trainee's bioelectrical activity;

filter means coupled to said suming amplifier for filtering the summed signals to obtain an output signal within a defined frequency range; and signal means coupled to said filter means for producing a visual signal and modulating the brightness of the visual signal responsive to the amplitude and phase of the summed bioelectrical activity so as to present to the trainee the visual signal which reflects the degree of phase parity and amplitude of the signals recorded from said at least two regions of the body.

17. An apparatus for measuring the bioelectrical activity such as muscle activity of at least two regions of the body of a human trainee and providing the trainee with a sensory signal in response to a combination of amplitude and the in-phase activity of each of the regions of the body comprising, a plurality of electrical contacts for coupling to the body of the trainee, said contacts being disposed adjacent to at least two regions of the body, and to a neutral area of the trainee's body so as to obtain at least two signals from said contacts which correspond to each of said at least two regions of the body;

at least one amplifier coupled to said contact for amplifying said at least two signals;

a summing amplifier coupled to said at least one amplifier for summing the in-phase signals of the amplified signals to produce a phase relevant measure of the trainee's bioelectrical activity;

filter means coupled to said summing amplifier for filtering the summed signals to obtain an output signal within a defined frequency range; and audio signal means for producing an auditory signal and modulating the volume of the auditory signal responsive to the amplitude and phase of the summed bioelectrical activity so as to present to the trainee an auditory signal which reflects the degree of phase parity and amplitude of the signals recorded from said at least two body regions.

* * * * *